(12) United States Patent
Sivebæk

(10) Patent No.: US 9,187,634 B2
(45) Date of Patent: Nov. 17, 2015

(54) LOW FRICTION SYSTEMS AND DEVICES

(75) Inventor: Ion Marius Sivebæk, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 384 days.

(21) Appl. No.: 12/373,939

(22) PCT Filed: Jul. 3, 2007

(86) PCT No.: PCT/EP2007/056680
§ 371 (c)(1),
(2), (4) Date: Feb. 26, 2009

(87) PCT Pub. No.: WO2008/015066
PCT Pub. Date: Feb. 7, 2008

(65) Prior Publication Data
US 2009/0177150 A1     Jul. 9, 2009

Related U.S. Application Data

(60) Provisional application No. 60/834,691, filed on Aug. 1, 2006.

(30) Foreign Application Priority Data

Jul. 31, 2006 (EP) ..................... 06118178

(51) Int. Cl.
| | | |
|---|---|---|
| A61M 5/31 | (2006.01) | |
| B32B 9/04 | (2006.01) | |
| B32B 27/36 | (2006.01) | |
| C08L 59/04 | (2006.01) | |

(Continued)

(52) U.S. Cl.
CPC .................. *C08L 59/04* (2013.01); *C08L 59/00* (2013.01); *C08L 59/02* (2013.01); *C08L 67/02* (2013.01); *C08L 69/00* (2013.01); *F16C 33/201* (2013.01); *A61M 5/31513* (2013.01); *A61M 2005/3131* (2013.01); *A61M 2205/0222* (2013.01); *C08L 83/04* (2013.01); *C08L 2555/40* (2013.01)

(58) Field of Classification Search
None
See application file for complete search history.

(56) References Cited

U.S. PATENT DOCUMENTS

| | | |
|---|---|---|
| 4,371,445 A | 2/1983 | Faigle |
| 4,879,331 A | 11/1989 | Endo et al. |

(Continued)

FOREIGN PATENT DOCUMENTS

| | | |
|---|---|---|
| CN | 2271969 Y | 1/1998 |
| DE | 10029533 | 12/2001 |

(Continued)

OTHER PUBLICATIONS

Cambridge Dictionaries Online: Lubricant; http://dictionary.cambridge.org/dictionary/british/lubricant . Retrieved on Apr. 7, 2012.*

(Continued)

*Primary Examiner* — Callie Shosho
*Assistant Examiner* — Coris Fung
(74) *Attorney, Agent, or Firm* — Leon Y. Lum

(57) ABSTRACT

Disclosed herein are compositions and systems having a low coefficient of friction. The low friction system comprises a first surface and a second surface, where the first surface comprises (i) a polycarbonate and a first additive, or (ii) a polybutylene terephthalate and a second additive; and the second surface comprises a polyoxymethylene and a third additive. The low friction compositions and systems are valuable for producing devices, such as medical devices.

1 Claim, 1 Drawing Sheet

(51) Int. Cl.
*C08L 59/00* (2006.01)
*C08L 59/02* (2006.01)
*C08L 67/02* (2006.01)
*C08L 69/00* (2006.01)
*F16C 33/20* (2006.01)
*A61M 5/315* (2006.01)
*C08L 83/04* (2006.01)

(56) References Cited

U.S. PATENT DOCUMENTS

| | | |
|---|---|---|
| 4,979,331 A | 12/1990 | Tanaka et al. |
| 5,641,824 A | 6/1997 | Forschirm |
| 6,112,950 A * | 9/2000 | Di Giovanni et al. ...... 222/402.1 |
| 6,492,307 B1 * | 12/2002 | Matsuo et al. ................. 510/120 |
| 6,602,953 B1 | 8/2003 | Horio et al. |
| 6,852,677 B2 | 2/2005 | Kurz et al. |
| 2002/0072706 A1 * | 6/2002 | Hiblar et al. ............. 604/101.01 |
| 2004/0035417 A1 * | 2/2004 | Ottolangui ................ 128/202.17 |
| 2004/0056054 A1 * | 3/2004 | Ottolangui .................... 222/544 |
| 2004/0199139 A1 * | 10/2004 | Fowles et al. ................. 604/414 |
| 2005/0137566 A1 * | 6/2005 | Fowles et al. ................. 604/412 |
| 2006/0025507 A1 * | 2/2006 | Moore et al. .................. 524/275 |
| 2006/0029795 A1 * | 2/2006 | Sawyer et al. ................ 428/339 |
| 2006/0111489 A1 | 5/2006 | Hase et al. |

FOREIGN PATENT DOCUMENTS

| | | |
|---|---|---|
| EP | 420564 | 4/1991 |
| EP | 705991 | 4/1996 |
| EP | 2049595 | 2/2008 |
| EP | 2050787 | 4/2009 |
| JP | 63-297453 | 12/1988 |
| JP | S6485665 A | 3/1989 |
| JP | H01270872 A | 10/1989 |
| JP | 05-57018 | 7/1993 |
| JP | 10-033674 | 2/1998 |
| JP | 2001-132757 A | 5/2001 |
| JP | 2004-339271 | 2/2004 |
| JP | 2006-143869 A | 6/2006 |
| JP | 2006-161928 A | 6/2006 |
| WO | 2005065626 A1 | 7/2005 |
| WO | WO 2006/042673 | 4/2006 |
| WO | WO 2007/145211 | 12/2007 |

OTHER PUBLICATIONS

Hu Xianguo, Polymer-Plastics Technology and Engineering (2000), vol. 39, No. 1, pp. 137-150.
English Language Machine Translation of JP 2004-339271, published Feb. 12, 2004.
English Language Machine Translation of JP 05-57018, published Jul. 30, 1993.

* cited by examiner

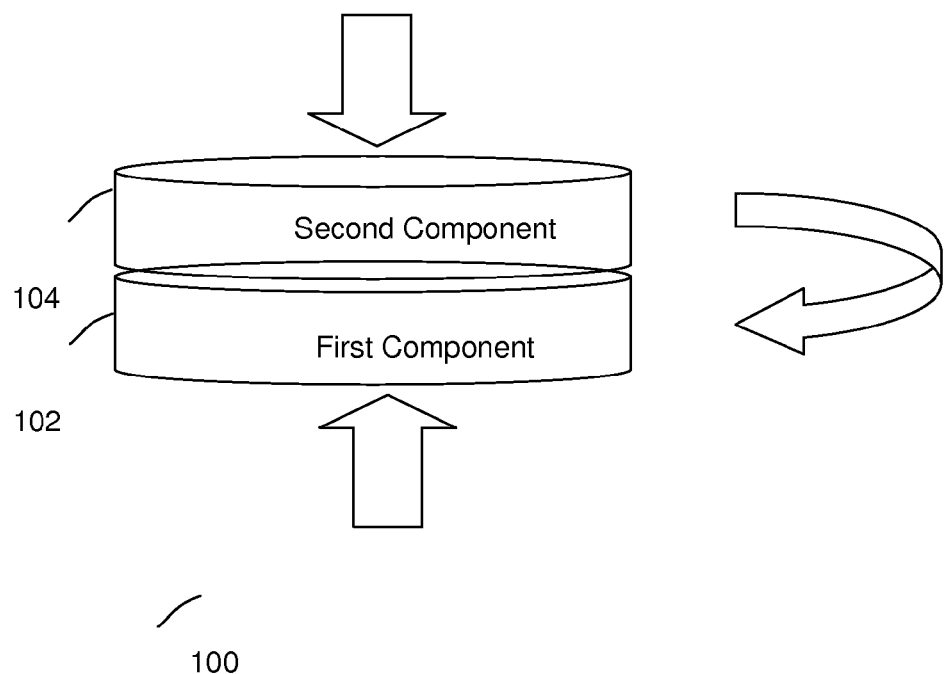

LOW FRICTION SYSTEMS AND DEVICES

CROSS-REFERENCE TO RELATED APPLICATIONS

This application is a 35 U.S.C. §371 national stage application of International Patent Application PCT/EP2007/056680 (published as WO 2008/015066), filed Jul. 3, 2007, which claimed priority of European Patent Application 06118178.0, filed Jul. 31, 2006; this application further claims priority under 35 U.S.C. §119 of U.S. Provisional Application 60/834,691, filed Aug. 1, 2006.

FIELD OF THE INVENTION

The present invention relates to low friction systems that are used for making sliding components, and further for producing devices. The invention also relates to compositions useful for producing such low friction systems and devices.

BACKGROUND OF THE INVENTION

When two materials slide against each other, it is often desirable to have a smooth contact between the surfaces of the materials so to reduce friction at the contact area. For a given pair of sliding surfaces, the magnitude of friction is generally given by the coefficient of friction. A lowering of the coefficient of friction generally leads to improved wear and reduced squeaking noises.

An important area of application where smoothly sliding materials are needed is in drug injection systems, which are commonly used to deliver therapeutic agents. Pen injectors constitute one class of drug injection systems. Pen injection components are commonly made of plastic materials, such as thermoplastics. The components are generally produced by injection moulding techniques. Pen injectors are widely used for delivering or injecting therapeutic agents into the body, example, a human body. Surfaces of a pen injection system that are in contact with each other slide during injection of the therapeutic agent into the human body. This leads to friction between the surfaces of the components that are in contact during the sliding motion. For example, the outer surface of a piston experiences sliding friction when it slides against a cylindrical tube of a pen injection system. The force with which a therapeutic agent is injected into a human body through a pen injection system is termed as dose force. One of the factors that determines the dose force in the pen injector is the friction between components of the pen injector that slide against each other. Therefore, if friction can be reduced, the dose force can also be reduced advantageously, thereby leading to a smoother operation and longer use of the injection system.

The known pen injector components exhibit a relatively high coefficient of friction when they slide against each other. Further, the components manufactured by commonly known techniques, such as injection moulding, require extensive running in, external lubrication, or both to obtain an instantaneous low coefficient of friction between them.

Therefore, there is a need for a system having components having a low coefficient of friction, that is, a coefficient of friction of less than 0.06 when measured using a contact pressure of 3.0 MPa (megapascals) and a sliding speed of 0.02 meters per second. Further, there is a need for methods for producing a low friction system that exhibits a low coefficient of friction of less than or equal to 0.06, without subjecting the components to the extra steps of exhaustive running-in, external lubrication, or both. Furthermore, there is a need for a system wherein after additional external lubrication of one or both components' surface(s), the frictional force is not further reduced.

SUMMARY OF THE INVENTION

The invention provides low friction systems and devices having components that exhibit a low coefficient of friction when there is relative motion between the components.

In one aspect, the invention provides a system comprising a first surface comprising: (i) a polycarbonate and a first additive, or (ii) a polybutylene terephthalate and a second additive; and a second surface comprising a polyoxymethylene and a third additive.

In another aspect, the invention provides a system comprising device comprising a first component in surface contact with a second component, the first component comprising: (i) a polycarbonate comprising a first additive, or (ii) a polybutylene terephthalate comprising a second additive; and the second component comprising a polyoxymethylene comprising a third additive.

In still another aspect, a method for producing a device comprises: forming a first moulding composition comprising a polycarbonate and a first additive, or a polybutylene terephthalate and a second additive; forming a second moulding composition comprising a polyoxymethylene and a third additive; and moulding the first and second moulding compositions.

In still yet another aspect, the invention provides a composition comprising: (i) a polycarbonate and a first additive, or a polybutylene terephthalate and a second additive, which form a first component; and (ii) a polyoxymethylene and a third additive, which form a second component; wherein the first and the second components upon mutual contact form a low friction system.

The systems and devices disclosed herein have a low coefficient of friction, that is a coefficient of friction of less than or equal to 0.06, when measured using a contact pressure of 3.0 MPa and a sliding speed of 0.02 meters per second.

BRIEF DESCRIPTION OF THE DRAWINGS

FIG. 1 illustrates an exemplary low friction system comprising a first and a second component, which press and slide circularly against each other, in accordance with an embodiment of the invention.

DETAILED DESCRIPTION OF THE INVENTION

The invention provides systems and devices having two or more surfaces comprising certain combinations of polymer materials. Such surfaces upon contact and relative sliding motion have a low coefficient of friction, that is a coefficient of friction of less than or equal to 0.06, when measured using a contact pressure of 3.0 MPa and a sliding speed of 0.02 meters per second.

In one aspect of the invention is disclosed a system comprising a first surface comprising: (i) a polycarbonate and a first additive, or (ii) a polybutylene terephthalate and a second additive; and a second surface comprising a polyoxymethylene and a third additive.

In another embodiment, the present invention provides a system comprising: a first surface comprising a polycarbonate and a first additive; and a second surface comprising a polyoxymethylene and a third additive. In still another embodiment, the present invention provides a system comprising: a first surface comprising a polybutylene terephthalate and a second additive; and a second surface comprising a polyoxymethylene and a third additive.

The first additive is preferably a silicone. Silicones, also sometimes referred to as polysiloxanes, polyorganosiloxanes, or organosilicones, are polymers consisting of a silicon-oxygen backbone (—Si—O—Si—O—Si—O—) and substituted on the silicon atoms with organic groups, such as alkyl groups and/or aryl groups. Silicones are odorless, colorless, water-resistant, chemical-resistant, oxidation-resistant and stable at high temperatures, and do not conduct electricity. Silicones are available in various structural variations and in various molecular weights. By way of an example, silicones having methyl groups as the substituents, commonly known as polydimethylsiloxanes are readily available in a range of molecular weights and viscosity ranges. In an embodiment, silicone oils can be used as the first additive with the polycarbonate. The silicone oil and the polycarbonate are independently in a relative weight ratio from 0.001 to 0.05.

The third additive for use with the polyoxymethylene is preferably also a silicone as described above. In an embodiment, the first and the third additives can be the same silicone. In another embodiment, the first and the third additives can be different silicones. In still other embodiments, different silicone oils having the same organic substituents on the silicon, but different viscosity ranges can also be used.

In an embodiment, the first, second, and the third additives can all be the same silicone. In another embodiment, any two of the first, second, and the third additives can be the same silicone. In still another embodiment, the first, second, and the third additive can all be different silicones having the same organic substituents on the silicon atoms, but different viscosities or molecular weights. Other possible variations of combinations of molecular weight, substitution patterns, and viscosities based on the wide range of silicones known in the art are also possible.

The first surface comprising the polycarbonate and the first additive may further comprise a fourth additive. In another embodiment, the second surface comprising the polyoxymethylene and the third additive may further comprise a fifth additive. The fourth and the fifth additive may each independently comprise an ethylene polymer a fluorinated ethylene polymer, or combinations of the ethylene polymer and the fluorinated ethylene polymer. Thus, the fourth and the fifth additives may each be an ethylene polymer in an embodiment, an ethylene polymer and a fluorinated ethylene polymer, respectively, in another embodiment; and each a fluorinated ethylene polymer in still another embodiment. Other possible variations of these polymers can also be used. Moreover, the ethylene polymers and the fluorinated ethylene polymers can have the same molecular weight, or different molecular weights. Suitable ethylene polymers include ethylene homopolymers and copolymers. In an embodiment, polyethylene, abbreviated as PE is a suitable ethylene polymer for use with the polycarbonate and the first additive for the first surface. Suitable examples of fluorinated ethylene polymers include polytetrafluorethylene, abbreviated as PTFE. In another embodiment, a system comprising a first and a second surface is disclosed wherein the first surface comprises a polycarbonate, a silicone oil as the first additive, and a polyethylene as the fourth additive; or a polybutylene terephthalate and a second additive; and the second surface comprises a polyoxymethylene, a silicone oil as the first additive, and a polyethylene as the fifth additive.

In an embodiment, the ethylene polymer and the polyoxymethylene, and the ethylene polymer and the polycarbonate may be present independently in a weight ratio from 0.01 to 0.99. In another embodiment, the fluorinated ethylene polymer and the polyoxymethylene, and the fluorinated ethylene polymer and the polycarbonate may be present independently in a weigh ratio from 0.01 to 0.99.

The polycarbonate for forming the first surface may, in an embodiment, include any of the known polycarbonate homopolymers and copolymers. Polycarbonates are commercially valuable thermoplastic polymers which are generally produced using one or more aromatic bisphenols. Polycarbonates homopolymers and copolymers prepared using bisphenol A as a monomer or a comonomer are widely available, and may be used advantageously for forming the low friction systems of the present invention. In a particular embodiment, the polycarbonate forming the first surface is bisphenol A polycarbonate. Polycarbonates are available under various trade names, such as ALCOM®, ALFA-CARB®; ANJALON®, APEC®, ASTALON®, AXX-ISPC®, AZLOY®, BARLO®, BAYBLEND®, BEETLE® CALIBRE®, DECAR-GLAS®, ECOCARB®, IUPON®, NAXELL®, POLYGAL®, SERACARB®, TEKULON®, UL-TRATUF® and ZELUX®. Commercial manufacturers of polycarbonate include GE Plastics, Dow, BASF, Mitsubishi, Bayer, RTP Company, and Teijin Chemicals.

The polybutylene terephthalate which is suitable for use as an alternative material for the first surface may in principle be any type of a homopolymer or a copolymer. Any of the polybutylene terephthalates known in the art may be used. Polybutylene terephthalate is generally produced commercially by reacting 1,4-butylene glycol with terephthalic acid. Polybutylene terephthalate copolymers comprising structural units derived from other aliphatic diol comonomers, such as for example, ethylene glycol and 1,3-propanediol may also be used. Commercial manufacturers of polybutylene terephthalate include GE Plastics, Toray, BASF, and Ticona. Some examples of commercially available grades of polybutylene terephthalate include ACESTER®, VALOX®, ALCOM®, ALFATER®, ANJADUR®, ARNITE®, AZDEL®, AZMET®, BADADUR®, BAYFOL®, BEETLE®, BERGADUE®, BST®, CELANEX®, CRASTIN®, DAFNELOV®, DENITER®, DURANEX®, DURLEX®, DURMAX®, DYNACOM®, EKTAR®, ENDURAN®, ENPLAC®, ENSITEP®, GRILPET®, HAUZER®, HILOY®, HYNSIN®, KAIFA®, KOPLA®, LATER®, LEMAPET®, LUMAX®, LUPOX®, LUPOY®, LUTREL®, LUVOCOM®, MAXNITE®, NEVIESTER®, NIBLAN®, NOVADURAN®, ORGATER®, PALDUR®, PERLOX®, PERMASTAT®, PETLON®, PIBITER®, PLANAC®, POCAN®, POLYSHINE®, RADIFLAM®, RADITER®, RYNITE®, SCHULADUR®, SEGREGATE®, SERATEC®, SHINITE®, SPESIN®, TARALOX®, TECADUR®, TECDUR®, TECHSTER®, TISMO POTICON®, TOPEX®, TRIBIT®, TUFPET®, TYNEP®, ULTRADUR®, VAMPTER®, VANDAR®, VESTODUR®, VEXEL®, and WHISTATT®.

The polyoxymethylene (abbreviated herein as "POM") is also referred to commonly by other names, such as polyacetal and acetal polymer. In POM the repeating structural unit in the polymer chain is the oxymethylene group (—OCH2-). In an embodiment, polyoxymethylene copolymers may also be used. For example, a copolymer obtained by using a comonomer having one or more glycidyloxy groups may be used. POMs are available under various trade names such as HOSTAFORM® AMCEL®, CELCON®, DELRIN®, KEPITAL®, ENSITAL®, KOPLA®, PALFORM®, TEPCON® and ULTRAFORM®, Suppliers of POM include Ashley Polymers, DuPont company, RTP Company, and Shuman Plastics, Inc.

The fluorinated ethylene polymer may be any homopolymer or copolymer produced from an ethylene monomer having at least one fluorine atom. The fluorine atom may be a vinylic fluorine atom or form part of a fluoroalkyl group, such as a monofluoromethyl, difluoromethyl, trifluoromethyl, and perfluoroalkyl. For example, a poly(perfluoroalkylene ether) may be used. Mixtures of various fluorinated ethylene polymers may also be used. Polytetrafluoroethylene (commonly known as "PTFE", also known as Teflon® may also be used as a fluorinated ethylene polymer. It is generally obtained by polymerizing tetrafluoroethylene. PTFE is generally an inert polymer under normal conditions of use.

The ethylene polymer includes all types of polymers other than the fluorinated ethylene polymers described hereinabove. Suitable ethylene polymers include homopolymers and copolymers produced using ethylene as a monomer or a comonomer, respectively. Polyethylenes with or without chain branches may be used as a suitable fourth or fifth additive. Thus polyethylene homopolymers and copolymers known in the art may be used. Polyethylenes of varying densities are generally obtained by controlling the molecular weight and density of branching, such as long chain branching along the polymer backbone. Suitable ethylene polymers include ultra-high molecular weight polyethylenes, high density polyethylenes, high density cross-linked polyethylenes, cross-linked polyethylenes, low density polyethylenes, linear low density polyethylenes, and very low density polyethylenes. Polyethylenes having a density of greater than or equal to 0.94 grams per cubic centimeter are generally considered as high density polyethylenes. Low density polyethylenes are generally materials having a density of 0.91-0.94 grams per cubic centimeter. Linear low density polyethylenes are generally materials having a density of 0.915-0.925 grams per cubic centimeter. Very low density polyethylenes are generally materials having a density of 0.88-0.915 grams per cubic centimeter.

In an embodiment, the ethylene polymer and the polycarbonate, and the ethylene polymer and the POM are independently present in a relative weight ratio from 0.01 to 0.99. In another embodiment, the fluorinated ethylene polymer and the polyoxymethylene, and the ethylene polymer and the polycarbonate are independently in a relative weight ratio from 0.01 to 0.99.

The materials described hereinabove provide for a composition for forming a low friction system having a low coefficient of friction that is less than or equal to 0.06. In an embodiment, a composition is provided which comprises: (i) a polycarbonate and a first additive, or a polybutylene terephthalate and a second additive, which form a first component; and (ii) a polyoxymethylene and a third additive which form a second component; wherein the first and the second components upon mutual contact form a low friction system. In another embodiment, the present invention provides a composition comprising a polycarbonate and a first additive, which form a first component; and a polyoxymethylene and a third additive, which form a second component; wherein the first and the second components upon contact form a low friction system. In still another embodiment, the present invention provides a composition comprising a polybutylene terephthalate and a second additive, which form a first component; and a polyoxymethylene and a third additive, which form a second component; wherein the first and the second components upon contact form a low friction system.

The materials and compositions described hereinabove are applicable for forming low friction systems and devices. In an embodiment, such a device comprises a first component in surface contact with a second component, wherein the first component comprises: (i) a polycarbonate and a first additive, or (ii) a polybutylene terephthalate and a second additive; and the second component comprises a POM comprising a third additive. In another embodiment, the device comprises a first component in surface contact with a second component, wherein the first component comprises a polycarbonate and a first additive; and the second component comprises a POM and a third additive. In still another embodiment, the device comprises a first component in surface contact with a second component, wherein the first component comprises a polybutylene terephthalate and a second additive; and the second component comprises a POM and a third additive.

The first and the second surfaces of the systems and the devices can be in relative motion in various ways. Thus the first surface may be stationary with respect to the second surface in an embodiment; and the second surface may be stationary with respect to the first surface in another embodiment. In still other embodiments, the first and the second surfaces may both be moving in the same direction at same or different speeds; the first and the second surfaces may both be moving in opposite directions at same or different speeds. When the surfaces slide relative to each other while maintaining contact, friction is produced at the contact zone. In accordance with an exemplary embodiment of the present invention, the contact zone has a coefficient of friction less than or equal to 0.06 when the two surfaces are in relative motion with respect to each other. FIG. 1 illustrates an exemplary system 100 having a first surface 102 that slides against a second surface 104, in accordance with an embodiment of the invention. Non-limiting examples of chemical compositions that can be used for the first surface 102 and the second surface 104 to form low friction systems having a coefficient of less than or equal to 0.06 are shown in Table 1, which is discussed further below herein.

The low friction systems are valuable for producing devices having sliding components that can operate more smoothly with less wear, such as devices that are used in healthcare and therapeutic applications. No external lubrication is needed, which leads to lower contamination of the materials with which the sliding surfaces come in contact. In an embodiment, injection systems or injection devices having a lower dosing force as compared to injection systems currently known in the art can be produced. Pen injectors having a lower dosing force for injecting drugs or medicaments, such as insulin can be produced. Other potential applications include use for making hinges for liquid crystal display devices, and pump bearings.

The low friction devices may be produced by a method which comprises: forming a first moulding composition comprising a polycarbonate and a first additive and optionally a fourth additive, or a polybutylene terephthalate and a second additive and optionally a fifth additive; forming a second moulding composition comprising a POM and a third additive; and moulding the first and second moulding compositions. Any of the various techniques known in the art for moulding plastic materials may be used. The invention is further illustrated with the following Examples.

EXAMPLES

For testing purposes, the first and second moulding compositions may be moulded to form discs or plates. Various amounts of the base polymer and the other ingredients for preparing the moulding compositions and the moulded specimens are shown in Table 1. The discs (test specimens), consisting of a lower rotary polymer specimen and an upper stationary polymer specimen were mounted on a testing device used for measuring the coefficient of friction. The tests were carried out by adapting the procedure described in ASTM standard D-3702 (re-approved in 2004) test method to those used for testing medical devices, by employing a contact pressure between the test specimens of 3 MPa and a sliding speed of 0.02 meters per second. The results are shown in Table 1, which also shows the chemical compositions of the first component 102 and the second component 104, and the measured coefficient of friction for each pair of components. In Table 1, the abbreviations mean the following: "PC"—polycarbonate; "PBT"—polybutylene terephthalate; "PE"—polyethylene; "COE"—coefficient of friction; "PC-Si"—a polycarbonate-siloxane block copolymer, commercially available as EXL 1112 grade; and "POM"—polyoxymethylene; "E" stands for Example; and "CE" stands for Comparative Example.

TABLE 1

| Expt No. | Weight Percent of Ingredients in First Component 102 | | | | Weight Percent of Ingredients in Second Component 104 | | | | COE |
|---|---|---|---|---|---|---|---|---|---|
| | Base Polymer | Silicone oil | PTFE | PE | Base Polymer | Silicone oil | PTFE | PE | |
| E-1 | PC | 2 | 18 | 0 | POM | 2 | 18 | 0 | 0.04 |
| E-2 | PC | 2 | 0 | 0 | POM | 2 | 5 | 0 | 0.06 |
| E-3 | PC | 2 | 0 | 0 | POM | 2 | 10 | 0 | 0.06 |
| E-4 | PC | 2 | 0 | 0 | POM | 2 | 18 | 0 | 0.06 |
| E-5 | PC | 2 | 5 | 0 | POM | 2 | 10 | 0 | 0.06 |
| E-6 | PC | 2 | 5 | 0 | POM | 2 | 18 | 0 | 0.06 |
| E-7 | PC | 2 | 10 | 0 | POM | 2 | 10 | 0 | 0.06 |
| E-8 | PC | 2 | 10 | 0 | POM | 2 | 18 | 0 | 0.06 |
| E-9 | PC | 2 | 0 | 0 | POM | 2 | 0 | 10 | 0.05 |
| E-10 | PC | 2 | 0 | 2 | POM | 2 | 0 | 10 | 0.05 |
| E-11 | PC | 2 | 0 | 5 | POM | 2 | 0 | 10 | 0.05 |
| E-12 | PC | 2 | 0 | 7 | POM | 2 | 0 | 10 | 0.05 |
| E-13 | PC | 2 | 0 | 40 | POM | 2 | 0 | 5 | 0.06 |
| E-14 | PBT | 2 | 0 | 0 | POM | 2 | 0 | 5 | 0.05 |
| E-15 | PBT | 2 | 0 | 0 | POM | 0 | 0 | 0 | 0.04 |
| E-16 | PBT | 2 | 0 | 0 | POM | 2 | 0 | 0 | 0.06 |
| CE-1 | PC-Si | 0 | 0 | 0 | POM | 0 | 0 | 0 | 0.16 |
| CE-2 | PBT | 0 | 0 | 0 | POM | 0 | 0 | 0 | 0.14 |

Inspection of the data in Table 1 shows that the various polymer compositions as shown can be used for producing low friction systems having a coefficient of friction of less than or equal to 0.06. Further, the low friction is achieved almost instantaneously with very little running in of the moulded components The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Any references cited herein are incorporated in their entirety.

This invention includes all modifications and equivalents of the subject matter recited in the claims appended hereto as permitted by applicable law. While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention, as described in the claims.

The invention claimed is:

1. A device comprising a first solid component in frictional surface contact with a second solid component,
    wherein the first solid component consists of a polybutylene terephthalate and silicone oil,
    wherein the second solid component consists essentially of a polyoxymethylene, and
    wherein friction at the surface contact due to relative motion in any direction between the first and the second components is less than or equal to about 0.06, when measured using a contact pressure of 3 MPa and a sliding speed of 0.02 meters per second.

* * * * *